(12) United States Patent
Ito et al.

(10) Patent No.: US 6,214,048 B1
(45) Date of Patent: Apr. 10, 2001

(54) BONE SUBSTITUTE PRODUCT AND METHOD OF PRODUCING THE SAME

(75) Inventors: Michio Ito; Hiroshi Yagasaki, both of Nagano (JP)

(73) Assignee: Matsumoto Dental College, Nagano (JP)

( * ) Notice: Subject to any disclaimer, the term of this patent is extended or adjusted under 35 U.S.C. 154(b) by 0 days.

(21) Appl. No.: 08/453,211

(22) Filed: May 30, 1995

Related U.S. Application Data

(62) Division of application No. 08/363,840, filed on Dec. 27, 1994, now abandoned, which is a continuation of application No. 08/015,918, filed on Feb. 10, 1993, now abandoned.

(30) Foreign Application Priority Data

Feb. 10, 1992 (JP) .................................................. 4-24106
Feb. 10, 1992 (JP) .................................................. 4-24111

(51) Int. Cl.$^7$ ...................................................... A61F 2/28
(52) U.S. Cl. .................................. 623/16.11; 623/23.72; 623/23.61
(58) Field of Search .............................. 623/16; 106/35; 424/423; 264/43

(56) References Cited

U.S. PATENT DOCUMENTS

| 4,772,591 | 9/1988 | Meisner | 424/423 |
|---|---|---|---|
| 5,167,961 | * 12/1992 | Lussi et al. | 424/423 |
| 5,180,426 | * 1/1993 | Sumita | 106/35 |
| 5,223,029 | * 6/1993 | Oonishi et al. | 106/35 |
| 5,290,558 | 3/1994 | O'Leary et al. | 623/16 |

FOREIGN PATENT DOCUMENTS

| 0329098 | * 2/1989 | (EP) . |
|---|---|---|
| 0 329 098 | 8/1989 | (EP) . |
| 2 101 036 | 3/1972 | (FR) . |
| 52-22026 | 2/1977 | (JP) . |
| 1-208347 | 8/1989 | (JP) . |
| 2 241 460 | 9/1990 | (JP) . |

OTHER PUBLICATIONS

Stedman's Medical Dictionary, 23$^{rd}$ Edition, ©1976 pp. 96, 664.*
Hawley's Condensed Chemical Dictionary, ©1987, 11$^{th}$ Edition, pp. 93, 621.*
Search Report for European patent application No. EP 93 10 1970.
Stedman's Medical Dictionary, 23rd Ed., pp. 96 and 664 (1976).
Hawley's Condensed Chemical Dictionary, 11th ED., pp. 93 and 621 (1987).

* cited by examiner

*Primary Examiner*—David J. Isabella
*Assistant Examiner*—Choon P. Koh
(74) *Attorney, Agent, or Firm*—Foley & Lardner

(57) ABSTRACT

A bone substitute material is prepared by firing and pulverizing animal bones into animal bone powder, mixing the animal bone powder and a divalent metal compound into a powdery mixture, and kneading the powdery mixture with chitosan sol. Alternatively, a bone substitute sheet is prepared by mixing at least one of apatite and animal bone powder with chitosan sol into a mixture, forming a preprocessed sheet of the mixture, and neutralizing the sheet by an aqueous solution of a compound. The bone substitute material and sheet have a pH value falling within a neutral range.

1 Claim, 4 Drawing Sheets

BONE SUBSTITUTE PRODUCT AND METHOD OF PRODUCING THE SAME

This application is a division, of application Ser. No. 08/363,840, filed Dec. 27, 1994, now abandoned, which is a continuation of application Ser. No. 08/015,918 filed Feb. 10, 1993, now abandoned.

BACKGROUND OF THE INVENTION

This invention relates to a bone substitute product, such as a material, a sheet, and a method of manufacturing the same. In particular, the bone substitute product is useful in dental, orthopedic, and plastic surgery fields as a filling or cushioning material for root canal filling, bone filling, a tooth support in pyorrhea alveolaris, and so on.

A bone substitute material of the type described is known which comprises a hardenable composition containing chitosan. The chitosan is well-known in the art as a natural abundant macromolecule. Such a hardenable composition is disclosed in Japanese Patent Prepublication No. 22026/1977. In order to manufacture the hardenable composition, an acidic aqueous solution of chitosan should be mingled or mixed with a basic water-hardenable inorganic material because the chitosan itself has a low solubility under a basic state or a non-acid state. As the basic water-hardenable inorganic material, use has generally been made of lime, Portland cement, alumina cement, or the like. The resultant composition is not lower than 9 in the pH value.

However, the above-mentioned conventional hardenable composition is improper for use in a human body because of such a high pH value.

Another conventional hardenable composition is disclosed in Japanese Patent Prepublication No. 208347/1989. The hardenable composition is manufactured by a mixture of an acidic aqueous solution of chitosan, particulate hydroxyapatite, zinc oxide and/or magnesium oxide. Due to presence of such hydroxyapatite, the hardenable composition exhibits an excellent affinity to a tooth and a bone and is hardened within a neutral range.

However, a very long time is required to create a bone when this hardenable composition is used as a bone substitute material.

In a dental field, dental cements have been extensively used for cementation of a restorative material, a temporary filling material, a root canal filling material, and so on. For example, as the dental cements, known are zinc phosphate cement, zinc oxide eugenol cement, and carboxylate cement. Such dental cements are prepared by mingling powder components and liquid components immediately before application and then hardened after lapse of 4 to 10 minutes.

However, such a dental cement has a pH value between 2 and 4 when a mixture of the powder component and the liquid component is prepared in the form of paste. In other words, the dental cement is acidic. When the dental cement is used in a human body for cementation, as mentioned above, dental pulp may be injured (inflammation, stimulation, and so on).

Consideration may be made as regards using the particulate apatite as a bone filling material. However, the particulate apatite often causes inflammation to occur in a gingiva. Specifically, the particulate apatite often migrates from an initial implant site and enters between a bone and the gingiva. This brings about inflammation in the gingiva under an occlusal pressure.

In addition, the hardenable composition containing the particulate apatite is not effective in creation of a bone because the particulate apatite is often migrated to be lost from the implant site.

SUMMARY OF THE INVENTION

It is therfore an object of this invention to provide a bone substitute product which is harmless and not toxic for organisms and which is quickly hardened in a neutral range after completion of chemical reaction.

It is another object of this invention to provide a bone substitute product which can avoid incidence of inflammation in a gingiva under the occlusal pressure and which is excellent in an ability of creating a bone.

It is still another object of this invention to provide a bone substitute product which will expect a wide variety of uses in a dental treatment.

It is yet another object of this invention to provide a method of producing a bone substitute product of the type described.

According to an aspect of this invention, there is provided a bone substitute material formed by kneading a powdery mixture of animal bone powder and a divalent metal compound together with chitosan sol which is prepared by dissolving chitosan by acid.

According to another aspect of this invention, there is provided a method of manufacturing a bone substitute material, the method comprising the steps of firing animal bones to leave inorganic components alone, pulverizing the animal bones into animal bone powder, mixing the animal bone powder and a divalent metal compound at a predetermined mixing ratio to make a powdery mixture, and kneading the powdery mixture with chitosan sol prepared by dissolving chitosan with acid.

According to still another aspect of this invention, there is provided a method of manufacturing a bone substitute material, the method comprising the steps of firing animal bones to leave inorganic components alone, pulverizing the animal bones into animal bone powder, mixing the animal bone powder, chemically synthesized apatite, and a divalent metal compound at a predetermined mixing ratio to form a powdery mixture, and kneading the powdery mixture with chitosan sol prepared by dissolving chitosan with acid.

According to yet another aspect of this invention, there is provided a bone substitute sheet manufactured by neutralizing a pre-processed sheet which comprises a mixture of apatite and chitosan sol prepared by dissolving chitosan with acid.

According to a further aspect of this invention, there is provided a bone substitute sheet manufactured by neutralizing a pre-processed sheet which comprises a mixture of animal bone powder and chitosan sol prepared by dissolving chitosan in acid.

According to another aspect of this invention, there is provided a method of manufacturing a bone substitute sheet, the method comprising the steps of mixing apatite with chitosan sol prepared by dissolving chitosan in acid to form a mixture of the apatite and the chitosan sol, shaping the mixture into a pre-processed sheet, and neutralizing the pre-processed sheet into the bone substitute sheet in an aqueous solution of a compound which contains at least one element selected from monovalent and divalent metal elements.

According to still another aspect of this invention, there is provided a method of manufacturing a bone substitute sheet, the method comprising the steps of firing animal bones to leave inorganic components in the fired animal bones, pulverizing the inorganic components into animal bone powder, mixing the animal bone powder with chitosan sol prepared by dissolving chitosan in acid to form a mixture of the animal bone powder and the chitosan sol, shaping the mixture to form a pre-processed sheet, and neutralizing the pre-processed sheet into the bone substitute sheet in an aqueous solution of a compound which contains at least one element selected from monovalent and divalent metal elements.

According to yet another aspect of this invention, there is provided a method of manufacturing a bone substitute sheet, the method comprising the steps of firing animal bones to leave inorganic components alone, pulverizing the fired animal bones into animal bone powder, mixing apatite, the animal bone powder, and chitosan sol prepared by dissolving chitosan in acid, to form a mixture of the apatite, the animal bone powder, and the chitosan sol, shaping the mixture into a pre-processed sheet, and neutralizing the pre-processed sheet into the bone substitute sheet in an aqueous solution of a compound which contains at least one element selected from monovalent and divalent metal elements.

DESCRIPTION OF THE PREFERRED EMBODIMENTS

A bone substitute product according to this invention is given in the form of a material or paste which will often be called a bone substitute material hereinunder. The bone substitute material is of a neutral, hardening type and serves as a bone inducing material. In a dental treatment, the bone inducing material can create a bone when implanted in the vicinity or in the interior of an existing bone.

First Embodiment

Now, description will be made as regards a bone substitute material according to a first embodiment of this invention. The bone substitute material comprises a neutral, uniformly hardening composition which is prepared by mixing a powder component and a liquid component into paste. The powder component consists of a mixture of animal bone powder and a compound of a divalent metal element. Such a compound may be an oxide of a divalent metal element (hereinafter simply referred to as a divalent metal oxide). The liquid component is an acidic aqueous solution of chitosan (hereinafter referred to as acidic chitosan sol).

The animal bone powder is mixed in the form of inorganic powder with the divalent metal oxide. It has been found out that animal bone powder implanted in organisms exhibits a bone inducing rate which is substantially twice as large as that of apatite. The animal bone powder is obtained by firing and pulverizing the animal bones from which human bones may be excluded. Anyway, selection can be made from a wide variety of animals living on the land and living under the sea. For example, bovine bones and swine bones may be used.

As the divalent metal oxide, zinc oxide and calcium oxide are used in this embodiment. Zinc oxide and calcium oxide serve as neutral agents. The hardening rate increases with an increase of an amount of zinc oxide. Either zinc oxide or calcium oxide may be solely used as the divalent metal oxide. Alternatively, zinc oxide may predominantly be used together with a small amount of calcium oxide or calcium silicate.

Acidic chitosan sol is prepared by dissolving chitosan with acid. The acid used to dissolve chitosan is selected from a group consisting of acetic acid, formic acid, lactic acid, malic acid, citric acid, adipic acid, tartaric acid, malonic acid, and the like.

Figure 1:
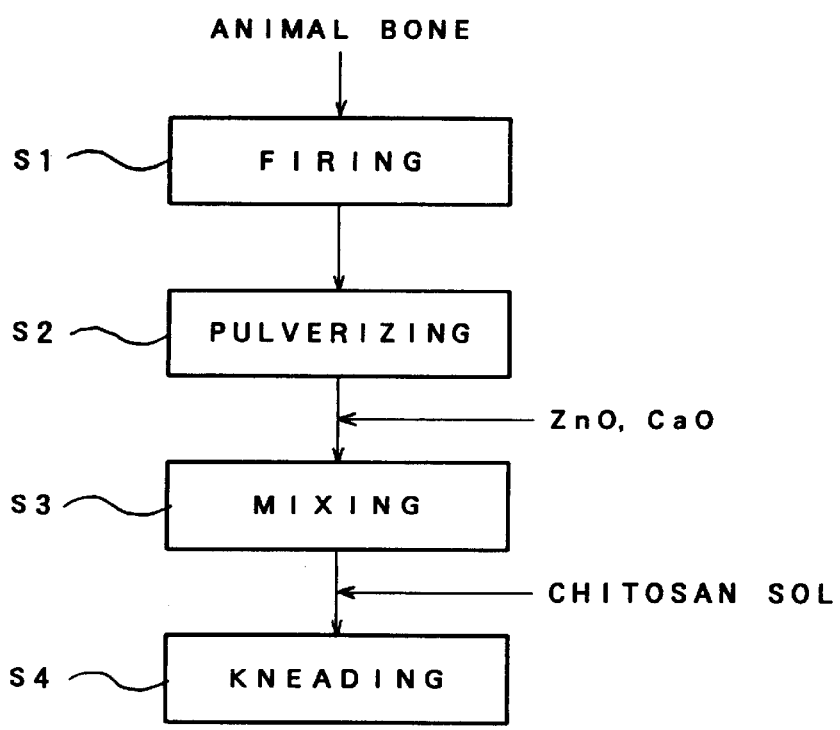
FIG. 1 is a flow chart for describing a method of manufacturing a bone substitute material according to a first embodiment of this invention.

Referring to FIG. 1, a method of manufacturing the above-mentioned bone substitute material will be described. The method comprises a firing step S1, a pulverizing step S2, a mixing step S3, and a kneading step S4.

At the firing step S1, animal bones are fired at a temperature between 800° C. and 1100° C. for 3 through 7 hours to leave inorganic components alone. At the pulverizing step S2, inorganic animal bones are pulverized into animal bone powder. At the mixing step S3, animal bone powder, zinc oxide, and calcium oxide are combined at a predetermined mixing ratio to make the powdery mixture. At the kneading step S4, the powdery mixture and acidic chitosan sol are kneaded into the paste.

Second Embodiment

A bone substitute material according to a second embodiment of this invention comprises a combination of a powdery mixture and acidic chitosan sol. The powdery mixture contains animal bone powder, apatite, zinc oxide, and calcium oxide. In this second embodiment also, one of zinc oxide and calcium oxide may be used alone. Alternatively, zinc oxide may be predominantly used. Acidic chitosan sol is prepared in a manner similar to the first embodiment.

Figure 2:
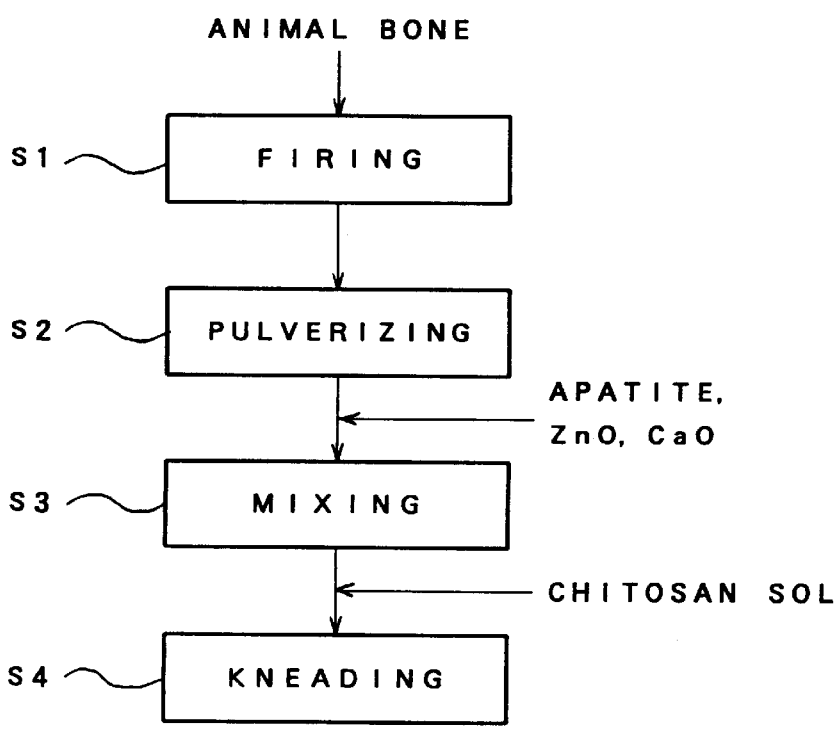
FIG. 2 is a flow chart for describing a method of producing a bone substitute material according to a second embodiment of this invention.

Referring to FIG. 2, description will proceed to a method of manufacturing the bone substitute material described above. The process comprises a firing step S1, a pulverizing step S2, a mixing step S3, and a kneading step S4.

At the firing step S1, animal bones are fired to leave inorganic components alone. At the pulverizing step S2, inorganic animal bones are pulverized into animal bone powder. At the mixing step S3, at least one particulate compound selected from the group consisting of apatite, hydroxyapatite, α-tricalcium phosphate and β-tricalcium phosphate, is mingled with animal bone powder, zinc oxide, and calcium oxide at a predetermined mixing ratio into the powdery mixture. At the kneading step S4, the powdery mixture and acidic chitosan sol are kneaded into the paste.

With this bone substitute material, no migration and no loss of the particulate apatite take place. This is because chitosan sol is transformed into gel to thereby fixedly confine the particulate apatite. Before chitosan is completely absorbed into an organism, osteoid is produced and substituted for a bone.

When bovine bone powder is used as inorganic animal bone powder, it is very effective to quickly create the bone.

This shows that the bovine bone powder serves as a bone inducing material which is excellent as compared with apatite. Bovine bone powder and apatite may be mingled at various ratios to form a great number of samples.

Now, various numerical values are offered below to exemplify mixing ratios and amounts of ingredients.

In the first embodiment, bovine bone powder is exclusively contained as animal bone powder in the powder component. No apatite is contained.

In the second embodiment, the powdery mixture has a mixing ratio of:

| | |
|---|---|
| calcium oxide | 0.5–35.0 wt % |
| zinc oxide | 0.5–35.0 wt % |
| bovine bone powder and apatite | 10–99 wt % |

In this invention, magnesium oxide is added to the powdery mixture as a neutral agent at a ratio of 0.05–20 wt %. In order to improve operability, a particle size of the bovine bone powder is not greater than 100 $\mu$m and preferably not greater than 74 $\mu$m. Such a particle size brings about an improvement of flowability in chitosan sol and facilitates filling operation into the implant site. The paste which is manufactured as mentioned above is hardened after lapse of 3 through 10 minutes. According to the inventor's experimental studies, it has been found out that the bone substitute material has a pH value between 6 and 8.

To prepare chitosan sol, chitosan of 0.05–0.125 g is dissolved in an acid of 0.05–0.255 g which includes distilled water or physiological saline solution of 2.0 cc.

The powdery mixture comprises ingredients as enumerated as follows.

| | |
|---|---|
| zinc oxide | 0.01–0.100 g |
| calcium oxide | 0.01–0.100 g |
| magnesium oxide | 0–0.005 g |
| bovine bone powder | 0.05–1.00 g |
| apatite | 0–1.00 g |

The use of calcium oxide is helpful to reduce the amounts of zinc oxide and magnesium oxide while the amount of apatite is increased. Depending upon a desired hardening rate, the mixing ratio is selected within the above-mentioned range. When the ratio of calcium oxide increases beyond the above-mentioned range, the pH value of the hardening composition exceeds 8. Accordingly, the amount of calcium oxide should not exceed the above-mentioned range.

Table 1 shows an experimental result of measurement of the hardening time of the bone substitute material. Three samples of the powder components were prepared which comprise amounts of bovine bone powder and apatite. Each of three samples was kneaded with first and second chitosan sols (A) and (B). Herein, it is to be noted that the first chitosan sol (A) was prepared by dissolving chitosan in malic acid while the second chitosan sol (B) was prepared by dissolving chitosan in malonic acid. Thus, six samples of the bone substitute material were manufactured in the form of paste and measured to estimate their properties. In Table 1, each sample is specified by a combination of the first and the second columns and is individually mixed with the first and the second chitosan sols (A) and (B) shown in the third and the fourth columns.

TABLE 1

| BOVINE BONE (g) | APATITE (g) | HARDENING TIME (A) | (minute) (B) |
|---|---|---|---|
| 0.40 | 0.00 | 150 or more | 6–8 |
| 0.30 | 0.10 | 80–90 | 6–8 |
| 0.20 | 0.20 | 40–60 | 5–7 |

As is clearly understood from Table 1, the hardening time is remarkably shortened by the use of the second chitosan sol (B) as compared with the use of the first chitosan sol (A). Thus, the malonic acid is very effective to shorten the hardening time in comparison with the malic acid.

At any rate, it is to be noted that the bone substitute material does not contain any toxic substance against the human body.

Figure 3:
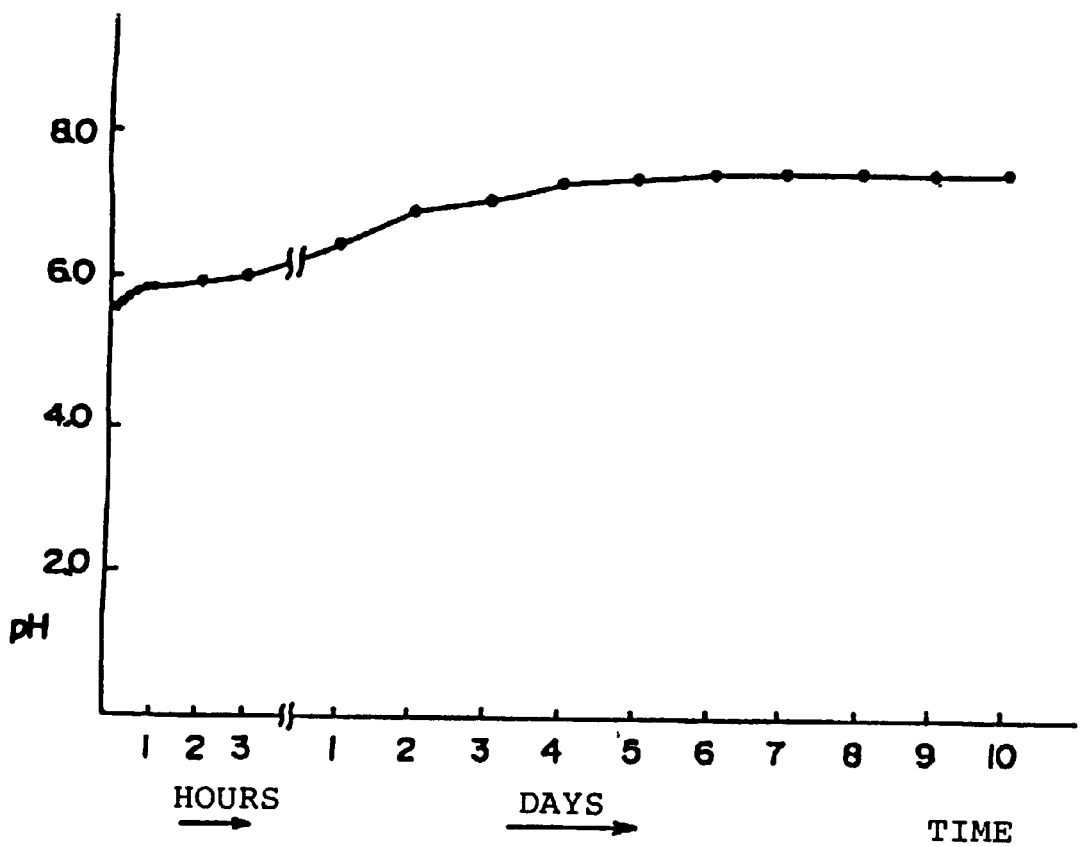
FIG. 3 is a graph for showing an experimental result of measurement of pH values of the bone substitute material according to the second embodiment of this invention.

As mentioned above, it is preferable that the resultant composition exhibits a neutrality in the pH value after completion of chemical reaction. Taking the above into consideration, the pH values were experimentally measured in connection with a specific one of the above-enumerated samples, as shown in FIG. 3. More particularly, the specific sample of the bone substitute material was manufactured by mixing 0.03 g of calcium oxide, 0.045 g of zinc oxide, 0.2 g of bovine bone powder, and 0.2 g of apatite to form the powdery mixture and by kneading the powdery mixture with the chitosan sol prepared by using 0.125 g of chitosan, 0.1 g of malonic acid, and 2.0 cc of physiological saline solution. As is obvious from FIG. 3, the bone substitute material was kept at a substantially constant pH value within a neutral range between 6 and 8 even after one week or more has passed.

Table 2 shows experimental results of measuring compressive strength as regards the bone substitute material enumerated in Table 1. Accordingly, the six samples have been prepared in the manner mentioned in conjunction with Table 1. However, it is to be noted in Table 2 that 0.03 g of CaO and 0.045 g of ZnO have been added to each sample.

TABLE 2

| BOVINE BONE (g) | APATITE (g) | COMPRESSIVE STRENGTH (kg/cm$^2$) | |
|---|---|---|---|
| | | (A) | (B) |
| 0.40 | 0.00 | 10.2 | 30.3 |
| 0.30 | 0.10 | 9.8 | 24.6 |
| 0.20 | 0.20 | 15.6 | 21.6 |

In order to observe growth or creation of tissue, provision was made about a particular one of the samples that was manufactured by mixing 0.2 g of bovine bone powder, 0.2 g of hydroxyapatite, 0.03 g of calcium oxide, and 0.045 g zinc oxide to form a powdery mixture and by kneading the powdery mixture with the chitosan sol prepared by the use of 0.125 g of chitosan, 0.1 g of malonic acid, and 2.0 cc of physiological saline solution. The particular sample was filled in a recess which was formed in a cranial bone of a rat. After lapse of four weeks, the rat was slaughtered for tissue observation. For this purpose, the cranial bone was stained by the use of a stain agent of eosine. As a result, growth of osteoid was clearly observed in the cranial bone.

A comparative example was prepared which comprised a small amount of hydroxyapatite without any bovine bone powder. A similar experiment was carried out in conjunction with the comparative sample also. Consequently, only a very little osteoid was observed in the cranial bone when such a comparative sample was used.

At any rate, each of the compositions according to the first and the second embodiments has a pH value between 6 and 8 after hardened. In other words, the resultant composition is hardened in the neutral range and is therefore harmless to the human body.

Accordingly, the bone substitute material never injures dental pulp and is excellent in creation of a bone. The bone substitute material is therefore useful in a root canal filling material, a bone filling material, bone cements, a tooth support in pyorrhea alveolaris, and so on.

The bone substitute material keeps a slight elasticity in a human body also. Therefore, it is possible to avoid inflammation of a gingiva due to an occlusal pressure, even if the bone substitute material is filled between the bone and the gingiva in order to reproduce a jaw bone.

Third Embodiment

Next, a bone substitute sheet product according to a third embodiment of this invention is manufactured in the form of a bone substitute sheet, as will be described. The bone substitute sheet is formed by a bone substitute material which is somewhat similar to that illustrated with reference to the first and the second embodiments. In this connection, the bone substitute sheet serves as either a bone filling material sheet or a bone inducing material sheet and is very effective in the dental treatment. Therefore, a wide variety of uses will be considered as regards the bone substitute sheet in the future.

Now, the bone substitute sheet is manufactured by preparing a pre-processed sheet formed by a combination of apatite and acidic chitosan sol and by neutralizing the pre-processed sheet in an aqueous solution of a compound which includes at least one element selected from monovalent and divalent metal elements. The bone substitute sheet thus obtained has a predetermined strength.

In the bone substitute sheet, apatite comprises a bone morphogenetic protein which is capable of creating a bone of an organism. In the example, chemically synthesized hydroxyapatite is used as such apatite and mixed with α-tricalcium phosphate, β-tricalcium phosphate, and the like in a manner to be described later to form the pre-processed sheet.

On the other hand, acidic chitosan sol is prepared in the manner similar to the aforementioned embodiments and has an antibacterial property.

The aqueous solution of the monovalent metal compound may be, for example, physiological saline solution which contains at least one of calcium chloride, sodium bicarbonate, and sodium polyphosphate.

As the divalent metal compound included in the solution, use is made of at least one of calcium oxide and calcium silicate.

Description will be made as regards a method of producing the bone substitute sheet more in detail with reference to FIG. 4.

Figure 4:
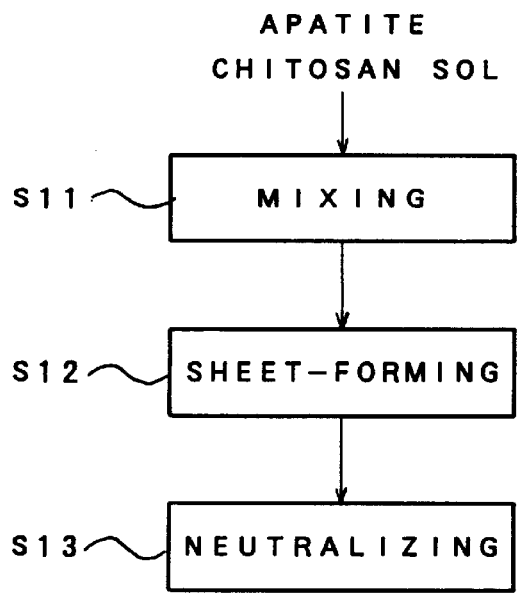
FIG. 4 is a flow chart for describing a method of producing a bone substitute sheet according to a third embodiment of this invention.

In FIG. 4, the method comprises a mixing step S11, a sheet-formation step S21, and a neutralizing step S31. At the mixing step S11, apatite and acidic chitosan sol are mixed into a mixture. At the sheet-formation step S21, the mixture is shaped into a sheet to form a pre-processed sheet. At the neutralizing step S31, the pre-processed sheet is neutralized by the aqueous solution containing at least one element selected from monovalent and divalent metal elements and is rendered into the bone substitute sheet.

The bone substitute sheet thus produced is cut into a plurality of sheet pieces each of which may have an optional size in correspondence to a diseased part.

For example, the sheet piece may be inserted between a jaw bone and a gingiva surrounding the jaw bone after operation for periodontitis in order to reconstruct the jaw bone and to prevent reccurrence of periodontitis.

Fourth Embodiment

A bone substitute sheet according to a fourth embodiment of this invention is manufactured from a pre-processed sheet formed by a combination of acidic chitosan sol and inorganic animal bone powder. The chitosan sol is prepared in a manner similar to that described in conjunction with the third embodiment. The inorganic animal bone powder is prepared by firing and pulverizing animal bones like in the first and the second embodiments. In this embodiment also, the pre-processed sheet is neutralized by an aqueous solution containing at least one element selected from monovalent and divalent metal elements and is rendered into the bone substitute sheet.

In other words, the bone substitute sheet thus obtained has a neutrality in the pH value and comprises a uniformly hardening composition which includes a mixture of animal bone powder and chitosan sol. As described above, addition of the inorganic animal bone powder is effective to increase bone inducing speed in comparison with inclusion of apatite alone. Although the bovine bone powder is used as animal bone powder in this embodiment, any other animal bones may be used to obtain the animal bone powder.

Figure 5:
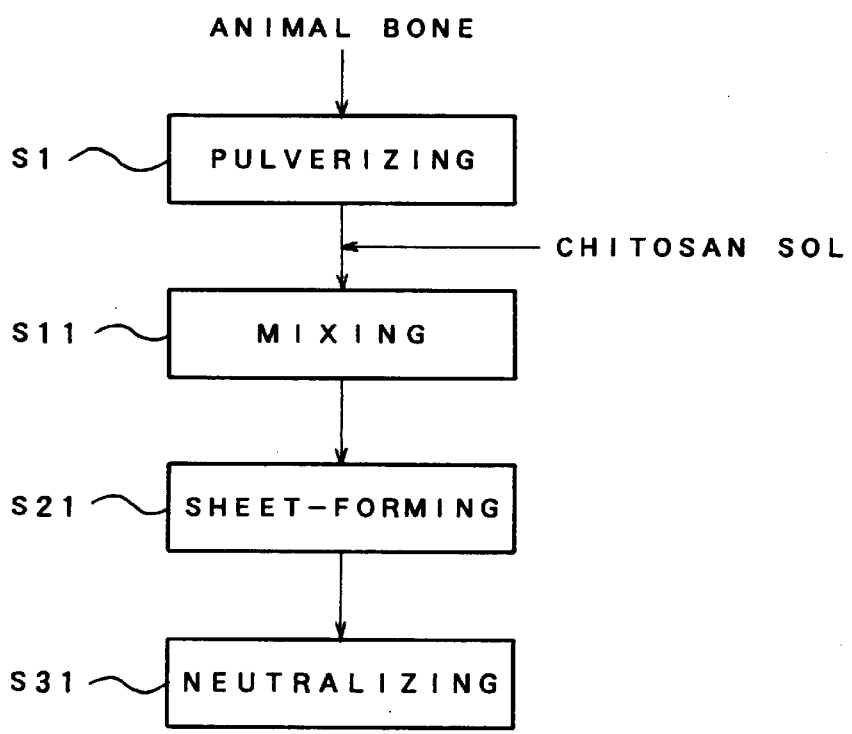
FIG. 5 is a flow chart for describing a method or producing a bone substitute sheet according to a fourth embodiment of this invention.

Referring to FIG. 5, description will be made more in detail as regards a method of manufacturing the bone substitute sheet according to the fourth embodiment of this invention. As shown in FIG. 5, the method comprises a pulverizing step S1, a mixing step S11, a sheet-formation step S21, and a neutralizing step S31. At the pulverizing step S1, animal bones are fired at a temperature between 800° C. and 1100° C. for 3 through 7 hours and pulverized into inorganic animal bone powder. At the mixing step S11, the inorganic animal bone powder is mixed with acidic chitosan sol which is previously prepared in the above-mentioned manner. As a result, a mixture of the inorganic animal bone powder and the acidic chitosan sol is formed in the mixing step S11. At the sheet-formation step S21, the mixture is shaped into a pre-processed sheet which is neutralized at the neutralizing step S31 by an aqueous solution containing at least one element selected from monovalent and divalent metal elements. Thus, the pre-processed sheet is rendered into the bone substitute sheet which comprises the inorganic animal bone powder and the chitosan sol without any apatite. The bone substitute sheet can be used in the manner mentioned with reference to the third embodiment.

Fifth Embodiment

A bone substitute sheet according to a fifth embodiment of this invention is manufactured from a pre-processed sheet which includes a combination of apatite, animal bone powder, and acidic chitosan sol. The pre-processed sheet is neutralized into the bone substitute sheet by an aqueous solution containing at least one element selected from monovalent and divalent metal elements.

Figure 6:
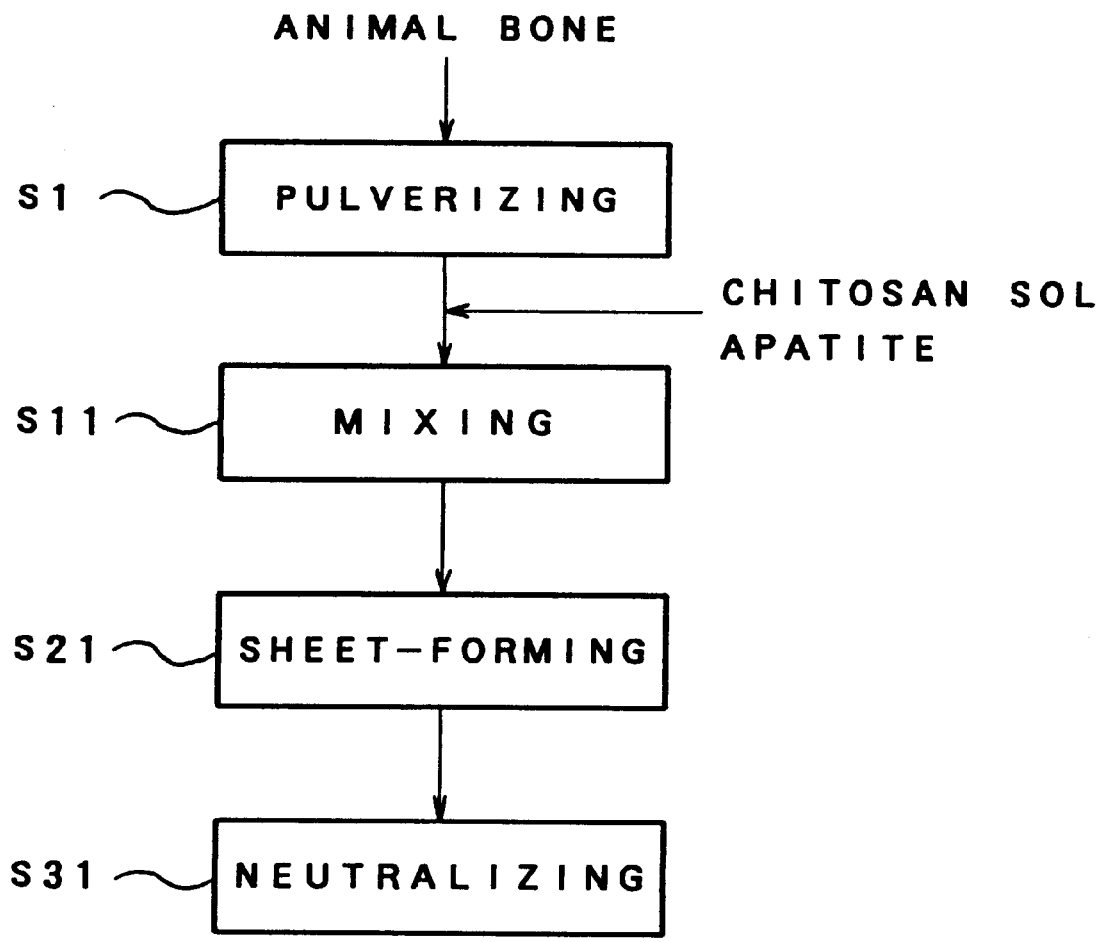
FIG. 6 is a flow chart for describing a method of producing a bone substitute sheet according to a fifth embodiment of this invention.

Referring to FIG. 6, description will be made as regards a method of manufacturing the bone substitute sheet according to the fifth embodiment. As illustrated in FIG. 6, the method comprises a pulverizing step S1, a mixing step S11, a sheet-formation step S21, and a neutralizing step S31. At the pulverizing step S1, animal bones are fired at a temperature between 800° C. and 1100° C. for 3 through 7 hours to leave inorganic components alone and thereafter pulverized into inorganic animal bone powder. In this example, the apatite and the acidic chitosan sol are previously prepared prior to the mixing step S11. At the mixing step S11, the animal bone powder, the apatite, and the acidic chitosan sol are mixed together into a mixture. At the sheet-formation step S21, the mixture is shaped into a pre-processed sheet. At the neutralizing step S31, the sheet is neutralized into the bone substitute sheet by an aqueous solution, as shown in FIGS. 4 and 5. The bone substitute sheet thus formed is cut into pieces by a knife or a pair of scissors, as mentioned before.

When the bone substitute sheet contains particulate apatite together with the chitosan sol, like in the third and the fifth embodiments, the particulate apatite is neither migrated nor lost from an implant site. This is because the chitosan sol is transformed into gel to desirably and fixedly confine the particulate apatite in the implant site. Under the circumstances, osteoid is effectively grown and substituted for a bone before the chitosan is absorbed into an organism.

It has been found out that use of the bovine bone powder promotes quick growth of the bone. This is because the bovine bone powder has a bone inducing rate considerably greater than that of the apatite as described before.

In the third embodiment, the bovine bone powder alone is added to the powder component without the apatite. In the fifth embodiment, both the bovine bone powder and the apatite may be contained at various ratios.

In any event, a particle size of the bovine bone powder may not be greater than 100 $\mu$m and may preferably be not greater than 74 $\mu$m.

Specifically, the bone substitute sheet can be obtained by hardening the paste in the aqueous solution of the neutralizing agents after lapse of 3 through 60 minutes. As a result, the pH value of the bone substitute sheet falls within a range between 6 and 8.

Now, consideration will be made as regards the compressive strength of the bone substitute sheet according to this invention. For measurement, a selected one of the bone substitute sheets was selected as a specimen which was manufactured in a following manner. At first, 0.5 g of the chitosan was dissolved with 0.5 g of the malic acid in 10 cc of the physiological saline solution to prepare the chitosan sol. The chitosan sol was mingled with 0.2 g of the hydroxyapatite and neutralized in an aqueous solution containing 2 wt % of CaO. As a result, the specimen had the compressive strength equal to 22.8 kg/cm$^2$ and had a pH value equal to 7.46. In the meanwhile, it has been confirmed that the pre-processed sheet had the pH value of 3.49 before neutralization. Thus, the neutralization is effective to adjust the pH value of the bone substitute sheet.

On the other hand, another bone substitute sheet was prepared as another specimen which was obtained from a chitosan sol prepared by dissolving 0.5 g of the chitosan and 0.5 g of the malonic acid in 10 cc of the physiological saline solution. The chitosan sol was mixed with 0.2 g of hydroxyapatite and neutralized in an aqueous solution containing 2 wt % of CaO. The resultant specimen had the compressive strength equal to 30.4 kg/cm$^2$ and a pH value of 7.32. The pre-processed sheet had the pH value of 3.03 before neutralization.

When 0.5 g of the chitosan is dissolved with 0.5 g of the malic acid, the malonic acid, or the citric acid in 10 cc physiological saline solution or distilled water, the apatite and the animal bone powder may be added within a range between 0.1 g and 10 g in total.

Tissue observation was carried out as regards one of the bone substitute sheet that belongs to the fourth embodiment and that will be called an additional specimen. The additional specimen was manufactured by kneading 0.5 g of the malonic acid, 0.2 g of the bovine bone powder, and the chitosan sol containing 0.5 g of the chitosan to form paste. The paste was formed into a pre-processed sheet which was neutralized by an aqueous solution containing 2 wt % of CaO. A gingiva surrounding a jaw bone of an adult dog was incised or dehisced to embed or implant, into the incised part, a piece of the bone substitute sheet which has a size of 3 mm×5 mm. Thereafter, the incised part was sutured. After lapse of four weeks, the incised part was taken out from the dog for tissue observation and was stained by the use of a stain agent of eosine. As a result, it has been confirmed that the bone has considerably grown in the implant site.

As described in conjunction with various embodiments, the resultant composition of the bone substitute product, such as the material, the sheet, has a pH value between 6 and 8. This means that the resultant composition is hardened in the neutral range and is therefore harmless to the human body, as repeatedly mentioned before.

Accordingly, the bone substitute sheet never injures dental pulp and is very helpful to create a bone. The bone substitute sheet can be used like the bone substitute material described with reference to the first and the second embodiments.

The bone substitute sheet can be cut into pieces of desired sizes in consideration of a size of the diseased part in the human body. Such a piece can be readily applied to the diseased part. Accordingly, the bone substitute sheet is effective in reconstruction of a human bone and in prevention of recurrence of periodontitis.

What is claimed is:

1. A bone substitute material comprising animal bone powder, at least one divalent metal compound and acidic chitosan sol, wherein said bone substitute material is a neutral, uniformly hardening composition, wherein said divalent metal compound is selected from the group consisting of calcium silicate, zinc oxide, calcium oxide and magnesium oxide and wherein said animal bone powder is bovine bone powder.

* * * * *